(12) United States Patent
Song et al.

(10) Patent No.: US 12,332,256 B2
(45) Date of Patent: Jun. 17, 2025

(54) ERYTHROCYTE SIMULATING PARTICLE, PREPARATION METHOD THEREFOR, AND QUALITY CONTROL OR CALIBRATOR CONTAINING SAME

(71) Applicant: Shenzhen Mindray Bio-Medical Electronics Co., Ltd., Shenzhen (CN)

(72) Inventors: Ruixia Song, Shenzhen (CN); Jian Xie, Shenzhen (CN)

(73) Assignee: Shenzhen Mindray Bio-Medical Electronics Co., Ltd., Shenzhen (CN)

( * ) Notice: Subject to any disclaimer, the term of this patent is extended or adjusted under 35 U.S.C. 154(b) by 1015 days.

(21) Appl. No.: 17/353,532

(22) Filed: Jun. 21, 2021

(65) Prior Publication Data
US 2021/0311080 A1 Oct. 7, 2021

Related U.S. Application Data

(63) Continuation of application No. PCT/CN2018/123529, filed on Dec. 25, 2018.

(51) Int. Cl.
*G01N 1/30* (2006.01)
*G01N 33/96* (2006.01)

(52) U.S. Cl.
CPC ............ *G01N 33/96* (2013.01); *G01N 1/30* (2013.01); *G01N 2001/305* (2013.01)

(58) Field of Classification Search
None
See application file for complete search history.

(56) References Cited

U.S. PATENT DOCUMENTS

| | | | |
|---|---|---|---|
| 4,342,740 | A | 8/1982 | Narra et al. |
| 2005/0136409 | A1 | 6/2005 | Leidig |
| 2012/0308985 | A1 | 12/2012 | Ryan et al. |
| 2016/0331885 | A1* | 11/2016 | Storr ............... B01D 71/68 |
| 2017/0176464 | A1* | 6/2017 | Xie ............... G01N 33/723 |

FOREIGN PATENT DOCUMENTS

| | | |
|---|---|---|
| CH | 500491 A | 12/1970 |
| CN | 101668854 A | 3/2010 |
| CN | 101881778 A | 11/2010 |
| CN | 102027132 A | 4/2011 |
| CN | 103267838 A | 8/2013 |
| CN | 103454410 A | 12/2013 |
| CN | 105717312 A | 6/2016 |
| CN | 107076766 A | 8/2017 |
| CN | 107723333 A | 2/2018 |
| CN | 108697802 A | 10/2018 |
| GB | 8606689 | 4/1986 |
| JP | H09248196 A | 9/1997 |
| WO | WO 9528915 A1 | 11/1995 |
| WO | 201716997 B1 | 10/2017 |

OTHER PUBLICATIONS

Shenzhen (English translation of CN105717312A) Erythrocyte simulation particle, preparation method and quality control material/calibratin material, Jun. 26, 2016, pp. 1-9. (Year: 2016).*
Ye et al., Particle-based simulations of red blood cells—a review, Journal of Biomechanics, 49, 2016, pp. 2255-2266/ (Year: 2016).*
Feng, Q., "The Progress in Pathological Diagnosis of Ascites", The Second Hospital of Hebei Medical University—Obstetrics and Gynecology, Dec. 2006, 4 pages.

* cited by examiner

*Primary Examiner* — Gary Counts
(74) *Attorney, Agent, or Firm* — Kory D. Christensen

(57) ABSTRACT

Erythrocyte simulating particles, a preparation method therefor, and a quality control or calibrator containing the erythrocyte simulated particles. The method for preparing erythrocyte simulating particles includes: performing oxidization and fixation treatments on erythrocytes by using an erythrocyte treatment solution that has a pH of 5.0-9.0 and an osmotic pressure of 300-800 Osm/kg·$H_2O$, wherein the erythrocyte treatment solution contains at least one oxidization agent selected from halogen oxygen acid salts and at least one fixation agent selected from aldehydes or acids; and washing the erythrocytes treated by the erythrocyte treatment solution and suspending the same in a preservation solution. The described method uses an environmentally friendly halogen oxygen acid salt as an oxidant, to obtain erythrocyte simulating particles that can be stored stably for a long time and have properties similar to natural erythrocyte particles in an erythrocyte detection channel.

17 Claims, 7 Drawing Sheets

(a1) (b1)

(a2) (b2)

ERYTHROCYTE SIMULATING PARTICLE, PREPARATION METHOD THEREFOR, AND QUALITY CONTROL OR CALIBRATOR CONTAINING SAME

CROSS-REFERENCE TO RELATED APPLICATIONS

This application is a continuation of International Application No. PCT/CN2018/123529, filed Dec. 25, 2018, the content of which is incorporated herein by reference.

TECHNICAL FIELD

The disclosure relates to erythrocyte simulating particles for a blood cell analyzer, a preparation method therefor, and a quality control or calibrator containing such erythrocyte simulating particles.

BACKGROUND

A blood cell analyzer is a fully automated biochemical analysis apparatus for analyzing parameters, including erythrocyte parameters, of a blood sample. In order to effectively monitor and calibrate erythrocyte detection results of the analyzer, erythrocyte simulating particles that are capable of effectively simulating characteristics of erythrocytes are required to prepare quality controls and standards.

Conventional methods for preparing erythrocyte simulating particles use aldehyde for fixation, which has the problem that volumes of cells change over time. The applicant has proposed a method for stabilizing red blood cells by fixation them with dichromate and aldehyde. However, the use of dichromate will cause environmental pollution problems.

Based on increasing requirements for reducing environmental pollutions, it is necessary to provide an environmentally friendly method for preparing erythrocyte simulating particles, and at the same time, the prepared erythrocyte simulating particles should be capable of remaining stable in terms of morphology, volume, etc. before the expiration period.

SUMMARY

For the problems in the prior art, the disclosure provides a method for preparing erythrocyte simulating particles, and thus provides erythrocyte simulating particles prepared thereby and a quality control/calibrator containing the erythrocyte simulating particles. The method of the disclosure and the erythrocyte simulating particles and the quality control/calibrator obtained thereby solve at least one of the problems mentioned above.

In a first aspect of the disclosure, according to a first implementation, provided is a method for preparing erythrocyte simulating particles, the method comprising:
  performing oxidization and fixation treatments on erythrocytes by using an erythrocyte treatment solution that has a pH of 5.0-9.0 and an osmotic pressure of 300-800 Osm/kg·$H_2O$, wherein the erythrocyte treatment solution contains at least one oxidization agent selected from halogen oxygen acid salts and at least one fixation agent selected from aldehydes or acids; and
  washing the erythrocytes treated by the erythrocyte treatment solution and suspending the same in a preservation solution.

The at least one oxidization agent of the disclosure is selected from the group consisting of hypohalous acid salts, halous acid salts, halic acid salts and perhalic acid salts of chlorine, bromine and iodine. Preferably, the at least one oxidization agent is selected from the group consisting of sodium salts and potassium salts of hypochlorous acid, chlorous acid, chloric acid, perchloric acid, bromic acid, iodic acid and periodic acid. Further preferably, the at least one oxidization agent is selected from the group consisting of sodium perchlorate, potassium perchlorate, sodium bromate, potassium bromate, sodium chlorate and potassium chlorate.

The at least one oxidization agent of the disclosure has a concentration of 0.01-20 g/L, preferably 0.05-10 g/L, and more preferably 0.05-5 g/L in the erythrocyte treatment solution.

According to one specific embodiment, the at least one oxidization agent is a perchlorate, especially sodium perchlorate, and has a concentration of 8-20 g/L, preferably 8-10 g/L in the erythrocyte treatment solution.

According to another specific embodiment, the at least one oxidization agent is a bromate, especially sodium bromate, and has a concentration of 0.25-2 g/L, preferably 0.25-1 g/L, and more preferably 0.25-0.5 g/L in the erythrocyte treatment solution.

According to yet another specific embodiment, the at least one oxidization agent is a chlorate, especially sodium chlorate, and has a concentration of 0.5-2 g/L, preferably 0.5-1 g/L in the erythrocyte treatment solution.

According to the disclosure, the at least one fixation agent is selected from the group consisting of formaldehyde, glutaraldehyde, glyoxal, methylglyoxal, p-trifluoromethyl benzaldehyde, paraformaldehyde, chromic acid, picric acid, tannic acid and acetic acid.

In the disclosure, the at least one fixation agent has a volume concentration of 0.01-0.5 vol % in the erythrocyte treatment solution.

In an embodiment, the erythrocyte treatment solution further contains a necessary buffer and an optional osmotic pressure regulator. Further, the erythrocyte treatment solution may also contain a preservative.

According to one specific embodiment, in the method of the disclosure, in the step of treatment by using the erythrocyte treatment solution, the erythrocyte treatment solution and the erythrocytes to be treated are mixed at a ratio of 1-2:1 to perform the treatment.

According to a second implementation, the disclosure further provides a method for preparing erythrocyte simulating particles, the method comprising:
  performing an oxidization treatment on erythrocytes by using a first erythrocyte treatment solution that has a pH of 5.0-9.0 and an osmotic pressure of 300-800 Osm/kg·$H_2O$, wherein the first erythrocyte treatment solution contains at least one oxidization agent selected from halogen oxygen acid salts;
  performing a fixation treatment on the erythrocytes by using a second erythrocyte treatment solution that has a pH of 5.0-9.0 and an osmotic pressure of 300-800 Osm/kg· $H_2O$, wherein the second erythrocyte treatment solution contains at least one fixation agent selected from aldehydes or acids; and
  washing the erythrocytes treated by the first erythrocyte treatment solution and the second erythrocyte treatment solution and suspending the same in a preservation solution.

Similarly, the at least one oxidization agent is selected from the group consisting of hypohalous acid salts, halous acid salts, halic acid salts and perhalic acid salts of chlorine, bromine and iodine. Preferably, the at least one oxidization agent is selected from the group consisting of sodium salts and potassium salts of hypochlorous acid, chlorous acid, chloric acid, perchloric acid, bromic acid, iodic acid and periodic acid. Further preferably, the at least one oxidization agent is selected from the group consisting of sodium perchlorate, potassium perchlorate, sodium bromate, potassium bromate, sodium chlorate and potassium chlorate.

In an embodiment, the at least one oxidization agent also has a concentration of 0.01-20 g/L, preferably 0.05-10 g/L, and more preferably 0.05-5 g/L in the first erythrocyte treatment solution.

In one specific embodiment, the at least one oxidization agent is a perchlorate, especially sodium perchlorate, and has a concentration of 8-20 g/L, preferably 8-10 g/L in the first erythrocyte treatment solution.

In another specific embodiment, the at least one oxidization agent is a bromate, especially sodium bromate, and has a concentration of 0.25-2 g/L, preferably 0.25-1 g/L, and more preferably 0.25-0.5 g/L in the first erythrocyte treatment solution.

In yet another specific embodiment, the at least one oxidization agent is a chlorate, especially sodium chlorate, and has a concentration of 0.5-2 g/L, preferably 0.5-1 g/L in the first erythrocyte treatment solution.

Similarly, the at least one fixation agent is selected from the group consisting of formaldehyde, glutaraldehyde, glyoxal, methylglyoxal, p-trifluoromethyl benzaldehyde, paraformaldehyde, chromic acid, picric acid, tannic acid and acetic acid.

The at least one fixation agent may have a volume concentration of 0.01-0.5 vol % in the second erythrocyte treatment solution.

In an embodiment, after the oxidization treatment, the erythrocytes subjected to the oxidization treatment are washed with a buffer, and then the fixation treatment is performed.

In an embodiment, the first and second erythrocyte treatment solutions also contain a necessary buffer and an optional osmotic pressure regulator. Further, the first and/or second erythrocyte treatment solution may further contain a preservative.

According to one specific embodiment, in the step of treatment by using the first erythrocyte treatment solution, the first erythrocyte treatment solution and the erythrocytes to be treated are mixed at a ratio of 1-2:1 to perform the oxidization treatment; and in the step of treatment by using the second erythrocyte treatment solution, the second erythrocyte treatment solution and the erythrocytes to be treated are mixed at a ratio of 1-2:1 to perform the fixation treatment.

In the first and second implementations of the disclosure, the preservation solution has a pH of 5.0-9.0 and an osmotic pressure of 300-800 Osm/kg· $H_2O$, and includes 0.01-10 g/L of a preservative and 0.01-5 g/L of a stabilizer.

In one specific embodiment, the preservative is selected from at least one of azide compounds, isothiazolinones and aminoglycoside antibiotics, and is capable of inhibiting microbial contamination in the erythrocyte simulating particles without affecting the stability of the erythrocyte simulating particles. The stabilizer is selected from imidazolidinyl ureas, and contributes to maintaining the stability of the erythrocyte simulating particles for a long time.

The preservation solution of the disclosure may also include a buffer and an optional osmotic pressure regulator. Further, the preservation solution may also include glucose.

In the above two implementations of the disclosure, the methods for preparing erythrocyte simulating particles of the disclosure further comprise performing a spheroidization treatment on the erythrocytes prior to treating the erythrocytes by using the (first) erythrocyte treatment solution.

The erythrocytes used in the methods for preparing erythrocyte simulating particles of the disclosure are derived from mammals, preferably from humans or mammals having erythrocytes with similar volumes to humans, such as monkeys or pigs.

A second aspect of the disclosure provides erythrocyte simulating particles. The erythrocyte simulating particles are prepared by any one of the methods according the first and second implementations of the first aspect mentioned above.

A third aspect of the disclosure provides a quality control or calibrator for a blood cell analyzer, wherein the quality control or calibrator comprises the erythrocyte simulating particles of the disclosure.

Specifically, the quality control or calibrator may further comprise at least one of leukocyte simulating particles, platelet simulating particles and nucleated erythrocyte simulating particles.

In the methods for preparing erythrocyte simulating particles according to the disclosure, an environmentally friendly halogen oxygen acid salt is used to change membrane protein conformation, thereby enhancing the stability of cell membrane skeleton while stabilizing hemoglobin in cells. In addition, in the disclosure, an aldehyde or acid fixation agent is used for fixing the cells to further maintain the stability of the cells, so as to obtain erythrocyte simulating particles that have properties similar to natural blood erythrocyte particles in an erythrocyte detection channel. The methods of the disclosure may achieve good (for example, in terms of cell morphology and volume) particle stability without performing a spheroidization treatment on erythrocytes, and avoid the use of heavy metals that are not environmentally friendly. Furthermore, the erythrocyte simulating particles prepared by the methods according to the disclosure are stored in a preservation solution containing a preservative and an imidazolidinyl urea stabilizer, which contributes to the long-term stability of the erythrocyte simulating particles.

DETAILED DESCRIPTION

Figure 1:
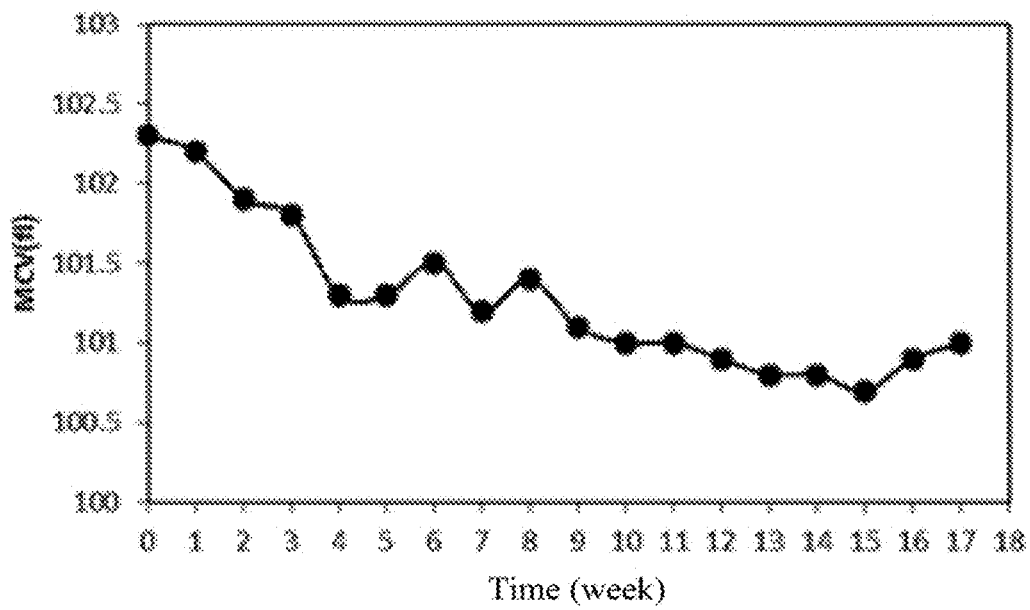
FIG. 1 is a graph of the mean erythrocyte volume over time of erythrocyte simulating particles prepared according to comparative example 1, as continuously measured in 18 weeks.

The technical solutions of embodiments of the disclosure will be described below clearly and completely in combination with specific embodiments and examples of the disclosure. Obviously, the embodiments described are merely some embodiments of the disclosure, not all embodiments of the disclosure. Based on the embodiments in the disclosure, all the other embodiments obtained by those of ordinary skill in the art without any creative efforts shall fall within the protection scope of the disclosure.

Throughout the specification, all terms used herein are intended to have their ordinary meaning in the art unless otherwise provided. Therefore, unless otherwise defined, all the technical and scientific terms used herein have the same meaning as commonly understood by those of skill in the art to which the disclosure belongs. In the event of a conflict, this specification takes precedence.

In this application, the terms "comprise", "include" or any other variation thereof are intended to cover non-exclusive inclusion, so that a method or product comprising a series of elements comprises not only explicitly recorded elements, but also other elements not explicitly listed, or elements inherent in implementing the method or product.

Unless otherwise specified, the singular forms "a/an" and "the/said" as used herein include the plural forms of the noun referred to.

In order to prepare erythrocyte simulating particles being capable of remaining stable for a long time, especially stable in volume, in an environmentally friendly way, the disclosure provides a method for preparing erythrocyte simulating particles. The method of the disclosure uses a halogen oxygen acid salt to perform an oxidization treatment on naturally derived erythrocytes, and further uses a fixation agent to perform a fixation treatment, so as to obtain stable erythrocyte simulating particles.

Since cells contain a large amount of protein, in order to prepare more stable erythrocyte simulating particles, the inventors have considered that in addition to a spheroidization treatment, a denaturation treatment is also required to change the conformation of cell membrane skeleton protein and hemoglobin. Moreover, common protein denaturants include strong acids, strong bases, heavy metal-containing salts, urea, acetone, etc. Various denaturants have different functional principles, but heavy metal salts have a significant effect on improving the stability of cell simulating particles. However, heavy metals bring serious pollution to environment. According to increasingly stringent environmental protection requirements, agents that are more environmentally friendly are needed to substitute for heavy metal salts. By a large number of experiments, the inventors have found that halogen oxygen acid salts can be used to denaturalize membrane protein (or further hemoglobin) in erythrocytes, and in the case of simultaneously performing a fixation treatment, a spheroidization treatment is not even necessary, and stable erythrocyte particles that behave, in a blood cell analyzer, similarly to erythrocytes in a fresh blood sample can also be obtained, thereby achieving the disclosure.

Compared with heavy metal oxyacid salts (such as dichromate or chromate) in the prior art, the oxidization agents of the disclosure avoid the use of heavy metals that pollute environment, and are more environmentally friendly. Moreover, the erythrocyte particles treated by the preferred embodiments of the disclosure are even more stable in volume.

Therefore, a method for preparing erythrocyte simulating particles of the disclosure includes:
performing oxidization and fixation treatments on erythrocytes by using an erythrocyte treatment solution that has a pH of 5.0-9.0 and an osmotic pressure of 300-800 Osm/kg·$H_2O$, wherein the erythrocyte treatment solution contains at least one oxidization agent selected from halogen oxygen acid salts and at least one fixation agent selected from aldehydes or acids; and
washing the erythrocytes treated by the erythrocyte treatment solution and suspending the same in a preservation solution.

Alternatively, as an alternative solution, a method for preparing erythrocyte simulating particles of the disclosure includes:
performing an oxidization treatment on erythrocytes by using a first erythrocyte treatment solution that has a pH of 5.0-9.0 and an osmotic pressure of 300-800 Osm/kg·$H_2O$, wherein the first erythrocyte treatment solution contains at least one oxidization agent selected from halogen oxygen acid salts;
performing a fixation treatment on the erythrocytes by using a second erythrocyte treatment solution that has a pH of 5.0-9.0 and an osmotic pressure of 300-800 Osm/kg·$H_2O$, wherein the second erythrocyte treatment solution contains at least one fixation agent selected from aldehydes or acids; and
washing the erythrocytes treated by the first erythrocyte treatment solution and the second erythrocyte treatment solution and suspending the same in a preservation solution.

That is, according to the methods of the disclosure, the oxidization treatment and the fixation treatment can be performed by one solution at the same time; or the oxidization treatment can be performed first, and the fixation treatment is then performed.

In the above two solutions of the disclosure, the halogen oxygen acid salts may include hypohalous acid salts, halous acid salts, halic acid salts or perhalic acid salts, especially alkali metal salts, of chlorine, bromine or iodine.

Preferably, the halogen oxygen acid salts of the disclosure may be selected from sodium hypochlorite, potassium hypochlorite, sodium chlorite, potassium chlorite, sodium chlorate, potassium chlorate, sodium perchlorate, potassium perchlorate, sodium bromate, potassium bromate, sodium iodate, potassium iodate, sodium periodate and potassium periodate. Further preferably, the halogen oxygen acid salts are selected from sodium perchlorate, potassium perchlorate, sodium bromate, potassium bromate, sodium chlorate and/or potassium chlorate. Most preferably, the halogen oxygen acid salts are selected from bromates, especially sodium bromate.

The at least one oxidization agent of the disclosure has a concentration of 0.01-20 g/L, preferably 0.025-10 g/L, more preferably 0.025-5 g/L and further preferably 0.025-2 g/L in the erythrocyte treatment solution.

Since different oxidization agents differ in oxidization capacity, in order to achieve the desired effect, those skilled in the art may determine a suitable concentration range of different oxidization agents according to specific conditions.

Preferably, the oxidization agent may be, for example, a perchlorate, especially sodium perchlorate, which may have a concentration of 8-20 g/L, preferably 8-10 g/L in the erythrocyte treatment solution; a bromate, especially sodium bromate, which has a concentration of 0.25-2 g/L, preferably 0.25-1 g/L, and more preferably 0.25-0.5 g/L in the erythrocyte treatment solution; or a chlorate, especially sodium chlorate, which has a concentration of 0.5-2 g/L, preferably 0.5-1 g/L in the erythrocyte treatment solution.

A bromate, especially sodium bromate, is preferred in the disclosure. Due to a low treatment concentration of the bromate used, and in combination with the following fixation agent, erythrocyte simulating particles that are more stable (especially stable in volume) can be obtained. According to the following specific embodiments, it can be seen that the simulating particles that are obtained by treating erythrocyte particles with bromates at different concentrations have a volume change of only about 1 femtoliter in a continuous measurement experiment for 18 weeks.

In the above two solutions of the disclosure, the fixation agent may include an aldehyde or an acid. For example, the fixation agent may include one or more selected from the group consisting of formaldehyde, glutaraldehyde, glyoxal, methylglyoxal, p-trifluoromethyl benzaldehyde, paraformaldehyde, chromic acid, picric acid, tannic acid and acetic acid.

In the above two solutions of the disclosure, a volume concentration of the fixation agent in the treatment solution (the erythrocyte treatment solution for the first solution, and the second erythrocyte treatment solution for the second solution) may be in the range of 0.01-0.5 vol %.

The erythrocyte treatment solutions for the two solutions in the methods of the disclosure further include a necessary buffer and an optional osmotic pressure regulator, so as to achieve a suitable pH value and osmotic pressure.

In the disclosure, the buffer is not particularly limited, and may be any buffer suitable for erythrocytes, including citrate sodium, Tris, PBS, HEPES, etc., but is not limited thereto. Similarly, the osmotic pressure regulator is also not particularly limited. The suitable osmotic pressure regulator includes sodium chloride, sodium dihydrogen phosphate, potassium chloride, citrate sodium, etc., but is not limited thereto.

Concentrations of the buffer and the osmotic pressure regulator are selected, such that the erythrocyte treatment solution of the disclosure has an osmotic pressure in a range 300-800 Osm/kg· $H_2O$ and a pH value in a range of 5.0-9.0.

Further, the erythrocyte treatment solution of the disclosure may further contain a preservative, for example, an azide (such as sodium azide) and isothiazolinone (Casson), such as proclin series (such as proclin300 and proclin950), but is not limited thereto. The amount of the preservative is usually in a range of 0.01-10 g/L.

In the above two solutions of the disclosure, in the step of treating by using the erythrocyte treatment solution (including the first erythrocyte treatment solution and the second erythrocyte treatment solution if the oxidization treatment and the fixation treatment are performed separately) of the disclosure, the (first/second) erythrocyte treatment solution may be mixed with the erythrocytes to be treated at a ratio of 1-2:1 for the corresponding treatment. The treatment time is usually in a range of 1-3 hours.

In the preparation method of the second solution according to the disclosure, after the oxidization treatment, the erythrocytes subjected to the oxidization treatment are washed with a buffer, and then the fixation treatment is performed.

Furthermore, in the first solution, after the oxidization-fixation treatment, or in the second solution, after the fixation treatment, the erythrocytes subjected to the oxidization-fixation treatment or the fixation treatment may be washed with a buffer, and then the washed erythrocytes are suspended in the preservation solution.

The buffer for washing is also not particularly limited, and may include a citrate sodium buffer, a Tris buffer, a PBS buffer or a HEPES buffer. The buffer may also have a pH of 5.0-9.0 and an osmotic pressure of 300-800 Osm/kg·$H_2O$.

In the first and second solutions of the disclosure, similarly, the preservation solution has a pH of 5.0-9.0 and an osmotic pressure of 300-800 Osm/kg·$H_2O$.

According to one example, the preservation solution includes 0.01-10 g/L of a preservative and 0.01-5 g/L of a stabilizer.

Specifically, the preservative includes at least one selected from azides, isothiazolinones and aminoglycoside antibiotics; and the stabilizer includes at least one selected from imidazolidinyl ureas, and preferably contains at least one isothiazolinone preservative and at least one aminoglycoside antibiotic. The use of a combination of the preservative and the stabilizer mentioned above is more conducive to the long-term stability of the erythrocyte simulating particles prepared by the disclosure.

An example of azides is sodium azide.

Examples of Casson antibacterial agents include proclin series, such as proclin300 and proclin950.

Examples of aminoglycoside antibiotics include streptomycin sulfate, kanamycin sulfate, neomycin sulfate, etc.

Examples of imidazolidinyl ureas include imidazolidinyl urea, diazolidinyl urea, etc.

The preservation solution of the disclosure further includes a buffer and an optional osmotic pressure regulator. Further, the preservation solution may also include glucose.

The buffer and the osmotic pressure regulator are as described above.

The preservation solution of the disclosure contributes to the stable preservation of blood cell simulating particles including erythrocyte simulating particles.

In the above two solutions of the disclosure, the methods for preparing erythrocyte simulating particles of the disclosure further includes the step of performing a spheroidization treatment on the erythrocytes prior to performing the treatment on the erythrocytes by using the (first) erythrocyte treatment solution.

The step of performing the spheroidization treatment may be realized by using a suitable surfactant. In the disclosure, the type and concentration of the surfactant are not particularly limited, and the surfactant that can be used to perform a spheroidization treatment on erythrocytes without damaging the cells, and appropriate concentrations thereof may all be applied in the disclosure. Especially, an alkyl quaternary ammonium salt cationic surfactant or an alkyl sulfonate anionic surfactant is preferred, but is not limited thereto.

A specific surfactant and a treatment method may be those disclosed in Chinese patent application CN 105717312 A. The content of CN 105717312 A is incorporated herein by reference in its entirety.

The spheroidization treatment of the erythrocytes further contributes to keeping the cell morphology and volume stable during a subsequent treatment or long-term storage.

Of course, as described above, erythrocyte simulating particles having the desired performance can still be obtained by the disclosure without performing a spheroidization treatment.

The erythrocytes used in the methods for preparing erythrocyte simulating particles of the disclosure are natural erythrocytes from mammals, preferably from humans or mammals having erythrocytes with volumes similar to humans, such as monkeys or pigs, wherein human erythrocytes are more preferred.

The erythrocyte simulating particles obtained by the above methods may be used in a quality control or calibrator for a blood cell analyzer. The quality control or calibrator is used to simulate a human blood sample, so as to monitor and calibrate erythrocyte detection results of the analyzer. The quality control or calibrator for a blood cell analyzer usually further contains at least one of leukocyte simulating particles, platelet simulating particles and nucleated erythrocyte simulating particles.

The advantages of the disclosure are further illustrated by the specific embodiments below.

Comparative Example 1: Treatment Using a Heavy Metal Ion

Erythrocyte simulating particles were prepared according to the following steps.

(1) An erythrocyte treatment solution was prepared according to the table below.

| No. | Name of component | Amount of component |
| --- | --- | --- |
| 1 | Sodium azide | 10 g |
| 2 | Potassium dichromate | 0.625 g |
| 3 | Sodium chloride | 9 g |
| 4 | Formaldehyde | 0.5 ml |
| 5 | Pure water | 1 L |

The pH was 8.0, and the osmotic pressure was 400 Osm/kg · $H_2O$ (2) 20 ml of human anticoagulant blood was washed with physiological saline at least twice, and centrifuged until there were no excessive suspension cells in the supernatant, and the supernatant was discarded to obtain a blood sample containing erythrocytes. The blood sample containing erythrocytes was mixed with the above erythrocyte treatment solution at a volume ratio of 1:1, and after mixing evenly, the mixture was left to stand at room temperature for 1 hour for performing oxidization and fixation treatments on the erythrocytes.

(3) The erythrocytes subjected to the treatment in step (2) were washed with physiological saline for 3 times, and then the erythrocytes were suspended in a preservation solution that has a pH of 8.0 and an osmotic pressure of 350 Osm/kg·$H_2O$ to obtain erythrocyte simulating particles, which were stored at 2-8° C.

The preservation solution was prepared according to the table below.

| No. | Name of component | Amount of component |
| --- | --- | --- |
| 1 | Glucose | 10 g |
| 2 | Proclin 300 | 3 ml |
| 3 | Streptomycin sulfate | 0.2 g |
| 4 | Kanamycin sulfate | 0.2 g |
| 5 | Imidazolidinyl urea | 0.3 g |
| 6 | HEPES buffer | 1 L |

The erythrocyte simulating particles in comparative example 1 were subjected to a mean corpuscular volume (MCV) measurement continuously for 18 weeks by a blood cell analyzer, in which the erythrocyte simulating particles were detected at least twice a week, and the MCV detection results were averaged. The measurement results are as shown in FIG. 1. The MCV measurement during the whole measurement period has a range (difference between the maximum and minimum values) of 1.6 fl, and an SD (standard deviation) of 0.42.

Example 1: Treatment Using Sodium Perchlorate of about 8 g/L

Erythrocyte simulating particles were prepared according to the following steps.

(1) An erythrocyte treatment solution was prepared according to the table below.

| No. | Name of component | Amount of component |
| --- | --- | --- |
| 1 | Proclin 300 | 3 ml |
| 2 | Sodium perchlorate | 8 g |
| 3 | Glutaraldehyde | 0.5 ml |
| 4 | HEPES buffer | 1 L |

The pH was 8.0, and the osmotic pressure was 400 Osm/kg · $H_2O$ (2) A preservation solution was prepared according to the table below.

| No. | Name of component | Amount of component |
| --- | --- | --- |
| 1 | Glucose | 10 g |
| 2 | Proclin 300 | 3 ml |
| 3 | Streptomycin sulfate | 0.2 g |
| 4 | Kanamycin sulfate | 0.2 g |
| 5 | Imidazolidinyl urea | 0.3 g |
| 6 | HEPES buffer | 1 L |

The pH was 8.0, and the osmotic pressure was 350 Osm/kg · $H_2O$ (3) 20 ml of human anticoagulant blood was filtered, centrifuged to remove leukocytes and platelets, and washed with a HEPES buffer twice, and the supernatant was discarded, with packed erythrocytes remained, so as to obtain a blood sample containing erythrocytes. The blood sample containing erythrocytes was mixed with the above erythrocyte treatment solution at a volume ratio of 1:1, and after mixing evenly, the mixture was left to stand at room temperature for 3 hours for performing oxidization and fixation treatments on the erythrocytes.

(4) The erythrocytes subject to the treatment in step (2) were washed with a HEPES buffer for 3 times, and then the erythrocytes were suspended in the above preservation solution to obtain erythrocyte simulating particles, which were stored at 2-8° C.

Figure 2:
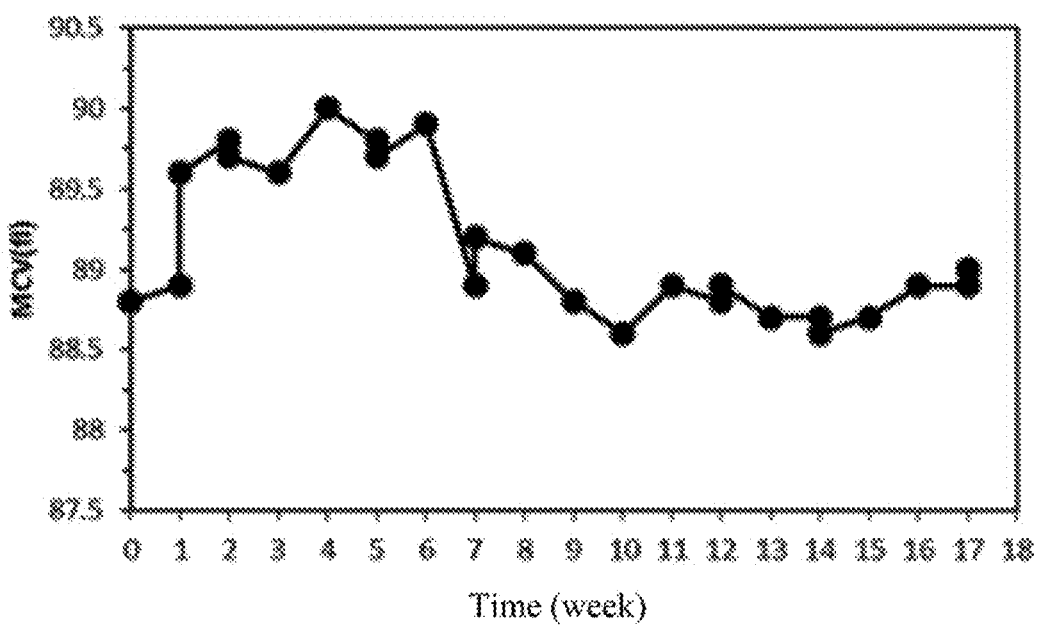
FIG. 2 is a graph of the mean erythrocyte volume over time of erythrocyte simulating particles prepared according to example 1, as continuously measured in 18 weeks.

The erythrocyte simulating particles in example 1 were subjected to a MCV measurement continuously for 18 weeks by the blood cell analyzer, in which the erythrocyte simulating particles were measured at least twice a week, and the MCV measurement results were averaged. The measurement results are as shown in FIG. 2. The MCV measured during the whole measurement period has a range (difference between the maximum and minimum values) of 1.4 fl, and an SD (standard deviation) of 0.46.

Example 2: Treatment Using Sodium Perchlorate of about 10 g/L

Erythrocyte simulating particles were prepared according to the following steps.

(1) An erythrocyte treatment solution was prepared according to the table below

| No. | Name of component | Amount of component |
|---|---|---|
| 1 | Proclin 300 | 3 ml |
| 2 | Sodium perchlorate | 10 g |
| 3 | Citrate sodium | 9 g |
| 4 | Formaldehyde | 0.5 ml |
| 5 | Pure water | 1 L |

The pH was 8.0, and the osmotic pressure was 400 Osm/kg · $H_2O$ (2) A preservation solution was prepared according to the formulation of example 1.

(3) 20 ml of human anticoagulant blood was filtered, centrifuged to remove leukocytes and platelets, and washed with a citrate sodium buffer twice, and the supernatant was discarded, with packed erythrocytes remained, so as to obtain a blood sample containing erythrocytes. The blood sample containing erythrocytes was mixed with the above erythrocyte treatment solution at a volume ratio of 1:1, and after mixing evenly, the mixture was left to stand at room temperature for 2 hours for performing oxidization and fixation treatments on the erythrocytes.

(4) The erythrocytes subjected to the treatment in step (2) were washed with a citrate sodium buffer for 3 times, and then the erythrocytes were suspended in the above preservation solution to obtain erythrocyte simulating particles, which were stored at 2-8° C.

Figure 3:
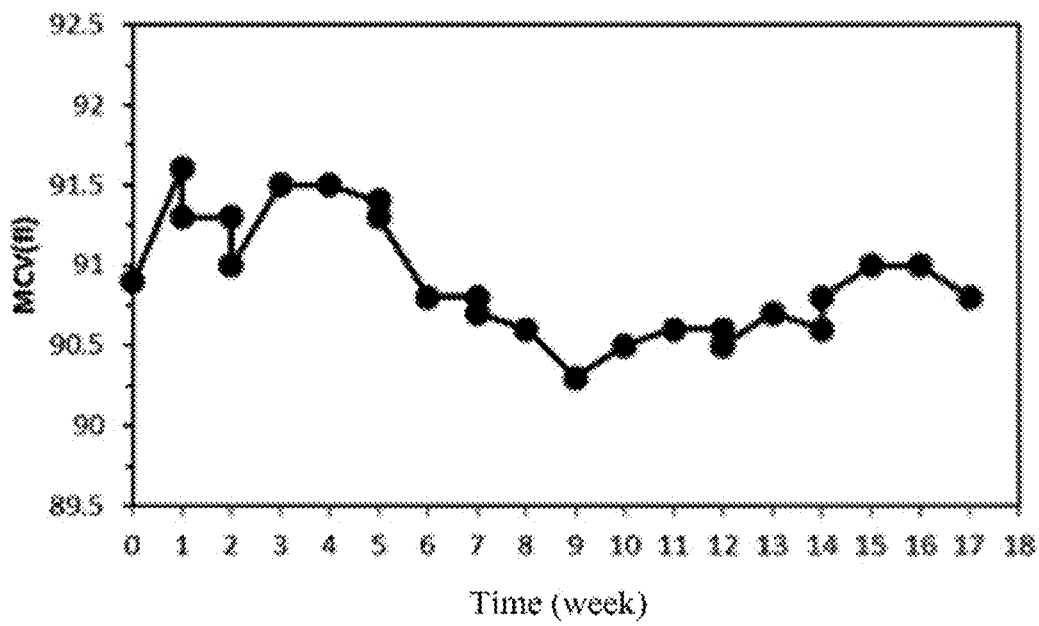
FIG. 3 is a graph of the mean erythrocyte volume over time of erythrocyte simulating particles prepared according to example 2, as continuously measured in 18 weeks.

The erythrocyte simulating particles in example 2 were subjected to an MCV measurement continuously for 18 weeks by the blood cell analyzer, in which the erythrocyte simulating particles were measured at least twice a week, and the MCV measurement results were averaged. The measurement results are as shown in FIG. 3. The MCV measured during the whole measurement period has a range (difference between the maximum and minimum values) of 1.3 fl, and an SD (standard deviation) of 0.38.

Example 3: Treatment Using Sodium Bromate of about 0.25 g/L

Erythrocyte simulating particles were prepared according to the following steps.

(1) An erythrocyte treatment solution was prepared according to the table below.

| No. | Name of component | Amount of component |
|---|---|---|
| 1 | Proclin 300 | 3 ml |
| 2 | Sodium bromate | 0.25 g |
| 3 | Glyoxal | 0.5 ml |
| 4 | PBS buffer | 1 L |

The pH was 8.0, and the osmotic pressure was 400 Osm/kg · $H_2O$ (2) A preservation solution was prepared according to the table below.

| No. | Name of component | Amount of component |
|---|---|---|
| 1 | Glucose | 10 g |
| 2 | Proclin 300 | 2 ml |
| 3 | Proclin 950 | 1 ml |
| 4 | Streptomycin sulfate | 0.2 g |
| 5 | Kanamycin sulfate | 0.2 g |
| 6 | Diazolidinyl urea | 2.0 g |
| 7 | PBS buffer | 1 L |

The pH was 7.4, and the osmotic pressure was 400 Osm/kg · $H_2O$ (3) 20 ml of human anticoagulant blood was filtered, centrifuged to remove leukocytes and platelets, and washed with a PBS buffer twice, and the supernatant was discarded, with packed erythrocytes remained, so as to obtain a blood sample containing erythrocytes. The blood sample containing erythrocytes was mixed with the above erythrocyte treatment solution at a volume ratio of 1:1, and after mixing evenly, the mixture was left to stand at room temperature for 1 hour for performing oxidization and fixation treatments on the erythrocytes.

(4) The erythrocytes subjected to the treatment in step (2) were washed with a PBS buffer for 3 times, and then the erythrocytes were suspended in the above preservation solution to obtain erythrocyte simulating particles, which were stored at 2-8° C.

Figure 4:
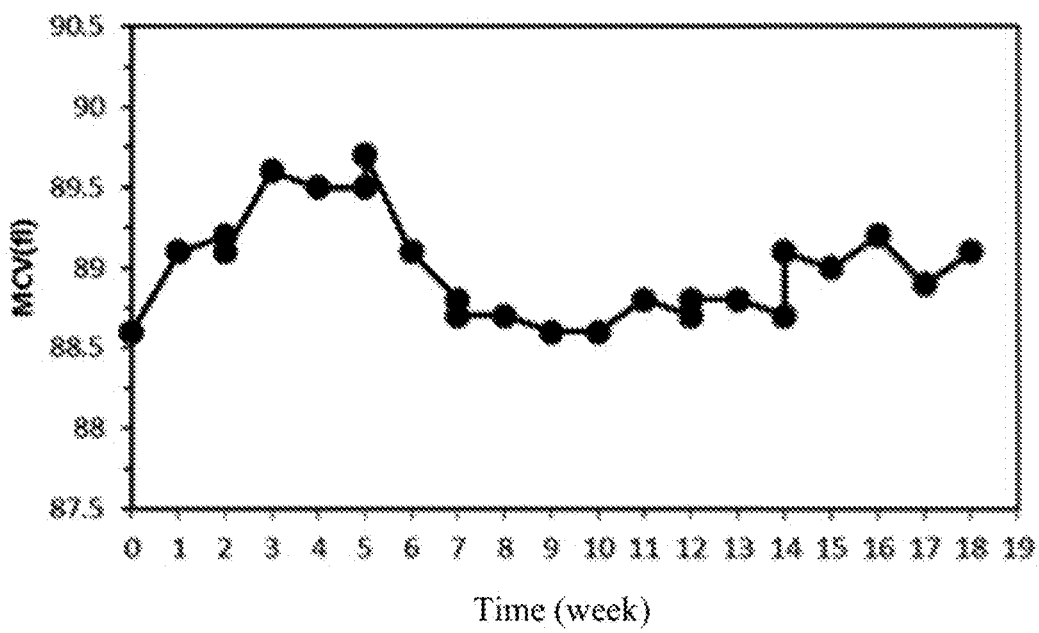
FIG. 4 is a graph of the mean erythrocyte volume over time of erythrocyte simulating particles prepared according to example 3, as continuously measured in 18 weeks.

The erythrocyte simulating particles in example 3 were subjected to an MCV measurement continuously for 18 weeks by the blood cell analyzer, in which the erythrocyte simulating particles were measured at least twice a week, and the MCV measurement results were averaged. The measurement results are as shown in FIG. 4. The MCV measured during the whole measurement period has a range (the difference between the maximum and minimum values) of 1.1 fl, and an SD (standard deviation) of 0.32.

Example 4: Treatment Using Sodium Bromate of about 0.5 g/L

Erythrocyte simulating particles were prepared according to the following steps.

(1) Erythrocyte treatment solutions A and B were prepared according to the table below.

| | No. | Name of component | Amount of component |
|---|---|---|---|
| Erythrocyte treatment solution A | 1 | Proclin 300 | 3 ml |
| | 2 | Sodium bromate | 0.5 g |
| | 3 | Tris buffer | 1 L |
| Erythrocyte treatment solution B | 1 | Proclin 300 | 3 ml |
| | 2 | Glutaraldehyde | 0.5 g |
| | 3 | Tris buffer | 1 L |

Both the erythrocyte treatment solution A and the erythrocyte treatment solution B had a pH of 8.0 and an osmotic pressure of 400 Osm/kg · $H_2O$.

(2) A preservation solution was prepared according to the formulation of example 3.

(3) 20 ml of human anticoagulant blood was filtered, centrifuged to remove leukocytes and platelets, and washed with a Tris buffer twice, and the supernatant was discarded, with packed erythrocytes remained, so as to obtain a blood sample containing erythrocytes. The blood sample containing erythrocytes was mixed with the above erythrocyte treatment solution A at a volume ratio of 1:1, and after mixing evenly, the mixture was left to stand at room temperature for 1 hour for performing an oxidization treatment on the erythrocytes.

(4) The erythrocytes subjected to the treatment in step (3) were washed with a Tris buffer at least twice, and then were suspended in a Tris buffer.

(5) The erythrocytes subjected to the treatment in step (4) were mixed with the above erythrocyte treatment solution B at a volume ratio of 1:1, and after mixing evenly, the mixture was left to stand at room temperature for 2 hours for performing a fixation treatment on the erythrocytes; and then the erythrocytes were suspended in the above preservation solution to obtain erythrocyte simulating particles, which were stored at a low temperature of 2-8° C.

Figure 5:
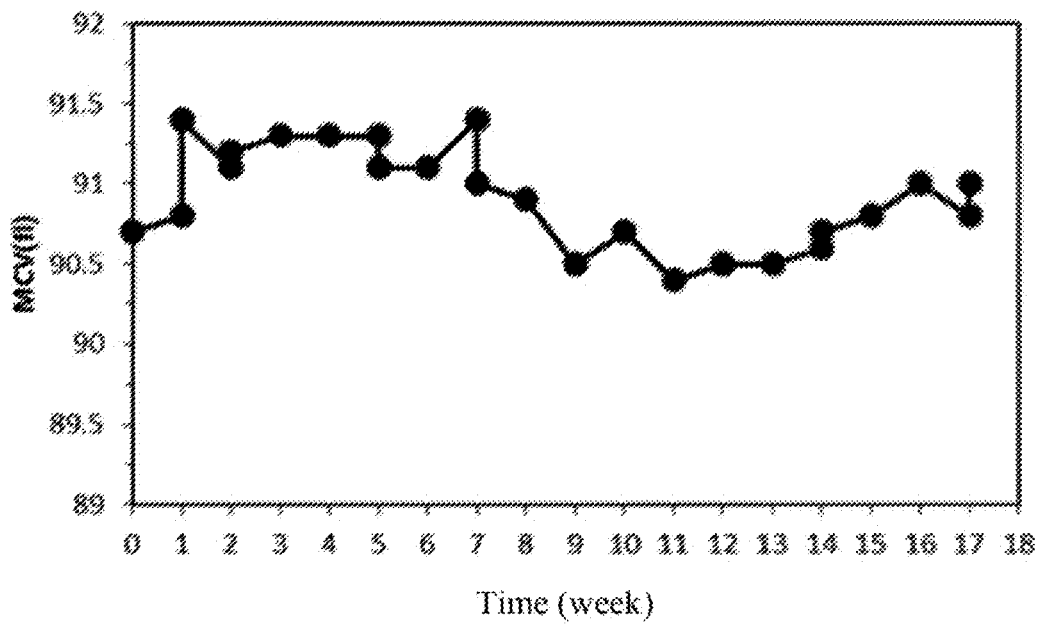
FIG. 5 is a graph of the mean erythrocyte volume over time of erythrocyte simulating particles prepared according to example 4, as continuously measured in 18 weeks.

The erythrocyte simulating particles in example 4 were subjected to an MCV measurement continuously for 18 weeks by the blood cell analyzer, in which the erythrocyte simulating particles were measured at least twice a week, and the MCV measurement results were averaged. The measurement results are as shown in FIG. 5. The MCV measured during the whole measurement period has a range (difference between the maximum and minimum values) of 1.0 fl, and an SD (standard deviation) of 0.31.

Example 5: Treatment Using Sodium Bromate of about 0.75 g/L

Erythrocyte simulating particles were prepared according to the following steps.

(1) An erythrocyte treatment solution was prepared according to the table below.

| No. | Name of component | Amount of component |
|---|---|---|
| 1 | Proclin 300 | 3 ml |
| 2 | Sodium bromate | 0.75 g |
| 3 | Paraformaldehyde | 0.4 ml |
| 4 | Sodium chloride | 9 g |
| 5 | Pure water | 1 L |

The pH was 8.0, and the osmotic pressure was 400 Osm/kg · $H_2O$ (2) A preservation solution was prepared according to the formulation of example 3.

(3) 20 ml of human anticoagulant blood was filtered, centrifuged to remove leukocytes and platelets, and washed with a Tris buffer twice, and the supernatant was discarded, with packed erythrocytes remained, so as to obtain a blood sample containing erythrocytes. The blood sample containing erythrocytes was mixed with the above erythrocyte treatment solution at a volume ratio of 1:1, and after mixing evenly, the mixture was left to stand at room temperature for 2 hours for performing oxidization and fixation treatments on the erythrocytes.

(4) The erythrocytes subjected to the treatment in step (3) were washed with a Tris buffer at least twice, and then the erythrocytes were suspended in the above preservation solution to obtain erythrocyte simulating particles, which were stored at 2-8° C.

Figure 6:
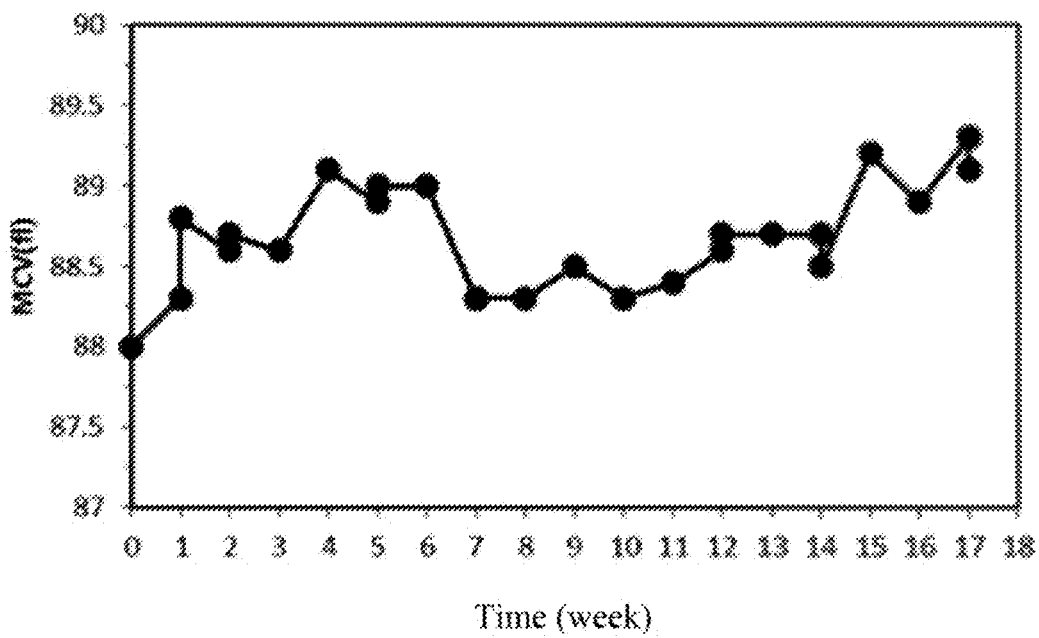
FIG. 6 is a graph of the mean erythrocyte volume over time of erythrocyte simulating particles prepared according to example 5, as continuously measured in 18 weeks.

The erythrocyte simulating particles in example 5 were subjected to an MCV measurement continuously for 18 weeks by the blood cell analyzer, in which the erythrocyte simulating particles were measured at least twice a week, and the MCV measurement results were averaged. The measurement results are as shown in FIG. 6. The MCV measured during the whole measurement period has a range (difference between the maximum and minimum values) of 1.3 fl, and an SD (standard deviation) of 0.33.

Example 6: Treatment Using Sodium Bromate of about 1 g/L

Erythrocyte simulating particles were prepared according to the following steps.

(1) An erythrocyte treatment solution was prepared according to the table below.

| No. | Name of component | Amount of component |
|---|---|---|
| 1 | Proclin 300 | 3 ml |
| 2 | Sodium bromate | 1 g |
| 3 | p-trifluoromethyl benzaldehyde | 0.6 ml |
| 4 | HEPES buffer | 1 L |

The pH was 8.0, and the osmotic pressure was 400 Osm/kg · $H_2O$ (2) A preservation solution was prepared according to the formulation of example 3.

(3) 20 ml of human anticoagulant blood was filtered, centrifuged to remove leukocytes and platelets, and washed with a HEPES buffer twice, and the supernatant was discarded, with packed erythrocytes remained, so as to obtain a blood sample containing erythrocytes. The blood sample containing erythrocytes was mixed with the above erythrocyte treatment solution at a volume ratio of 1:1, and after mixing evenly, the mixture was left to stand at room temperature for 2 hours for performing oxidization and fixation treatments on the erythrocytes.

(4) The erythrocytes subjected to the treatment in step (3) were washed with a HEPES buffer at least twice, and then the erythrocytes were suspended in the above preservation solution to obtain erythrocyte simulating particles, which were stored at 2-8° C.

Figure 7:
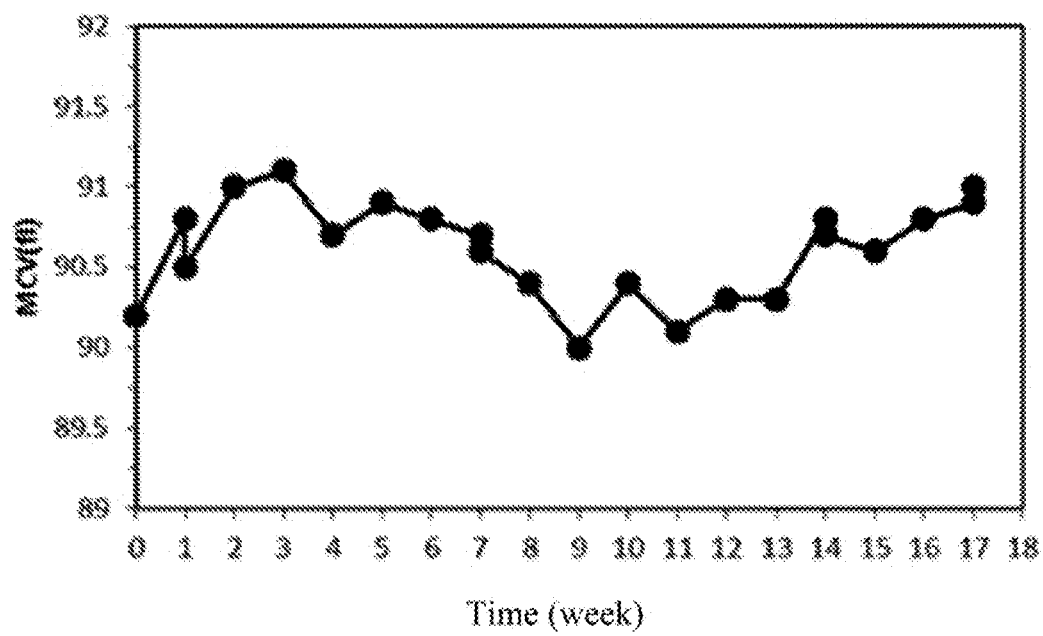
FIG. 7 is a graph of the mean erythrocyte volume over time of erythrocyte simulating particles prepared according to example 6, as continuously measured in 18 weeks.

The erythrocyte simulating particles in example 6 were subjected to an MCV measurement continuously for 18 weeks by the blood cell analyzer, in which the erythrocyte simulating particles were measured at least twice a week, and the MCV measurement results were averaged. The measurement results are as shown in FIG. 7. The MCV measured during the whole measurement period has a range (difference between the maximum and minimum values) of 1.1 fl, and an SD (standard deviation) of 0.31.

Example 7: Treatment Using Sodium Chlorate of about 0.5 g/L

Erythrocyte simulating particles were prepared according to the following steps.

(1) An erythrocyte treatment solution was prepared according to the table below.

| No. | Name of component | Amount of component |
|---|---|---|
| 1 | Proclin 300 | 3 ml |
| 2 | Sodium chlorate | 0.5 g |
| 3 | Methylglyoxal | 0.6 ml |
| 4 | HEPES buffer | 1 L |

The pH was 8.0, and the osmotic pressure was 400 Osm/kg · $H_2O$ (2) A preservation solution was prepared according to the table below.

| No. | Name of component | Amount of component |
| --- | --- | --- |
| 1 | Glucose | 10 g |
| 2 | Proclin 300 | 2 ml |
| 3 | Proclin950 | 1 ml |
| 4 | Kanamycin sulfate | 0.2 g |
| 5 | Neomycin sulfate | 0.2 g |
| 6 | Diazolidinyl urea | 0.8 g |
| 7 | HEPES buffer | 1 L |

The pH was 7.2, and the osmotic pressure was 300 Osm/kg · $H_2O$ (3) 20 ml of human anticoagulant blood was filtered, centrifuged to remove leukocytes and platelets, and washed with a HEPES buffer twice, and the supernatant was discarded, with packed erythrocytes remained, so as to obtain a blood sample containing erythrocytes. The blood sample containing erythrocytes was mixed with the above erythrocyte treatment solution at a volume ratio of 1:1, and after mixing evenly, the mixture was left to stand at room temperature for 3 hours for performing oxidization and fixation treatments on the erythrocytes.

(4) The erythrocytes subjected to the treatment in step (3) were washed with a HEPES buffer at least twice, and then the erythrocytes were suspended in the above preservation solution to obtain erythrocyte simulating particles, which were stored at 2-8° C.

Figure 8:
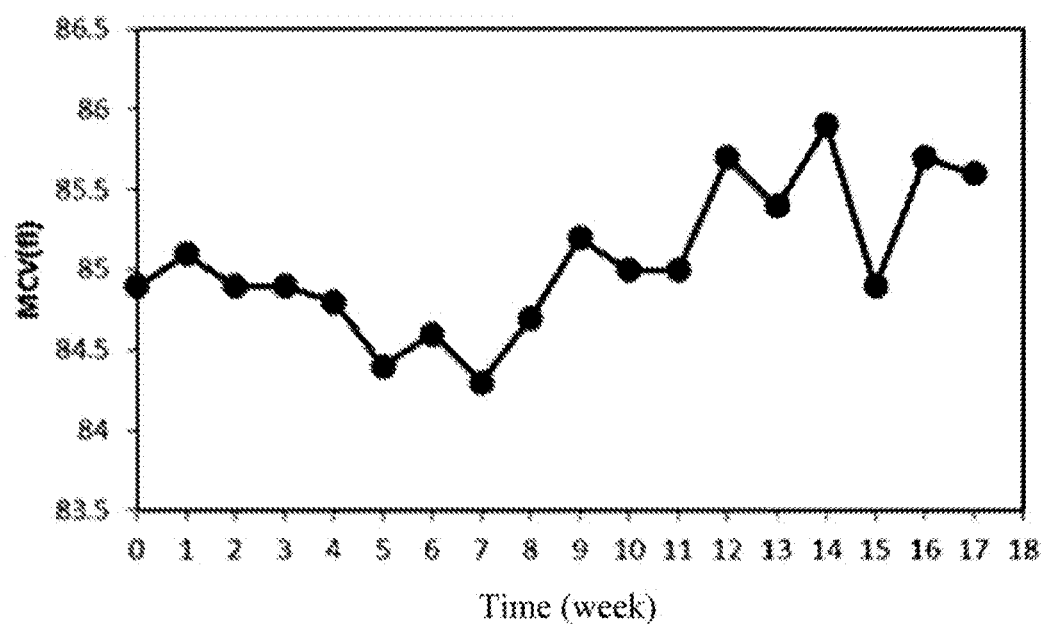
FIG. 8 is a graph of the mean erythrocyte volume over time of erythrocyte simulating particles prepared according to example 7, as continuously measured in 18 weeks.

The erythrocyte simulating particles in example 7 were subjected to an MCV erythrocyte simulating particles were measured at least twice a week, and the MCV measurement results were averaged. The measurement results are as shown in FIG. 8. The MCV measured during the whole measurement period has a range (difference between the maximum and minimum values) of 1.6 fl, and an SD (standard deviation) of 0.45.

Example 8: Treatment Using Sodium Chlorate of about 0.75 g/L

Erythrocyte simulating particles were prepared according to the following steps.

(1) An erythrocyte treatment solution was prepared according to the table below.

| No. | Name of component | Amount of component |
| --- | --- | --- |
| 1 | Proclin 300 | 3 ml |
| 2 | Sodium chlorate | 0.75 g |
| 3 | Glutaraldehyde | 0.5 ml |
| 4 | PBS buffer | 1 L |

The pH was 8.0, and the osmotic pressure was 400 Osm/kg · $H_2O$ (2) A preservation solution was prepared according to the formulation of example 7.

(3) 20 ml of human anticoagulant blood was filtered, centrifuged to remove leukocytes and platelets, and washed with a PBS buffer twice, and the supernatant was discarded, with packed erythrocytes remained, so as to obtain a blood sample containing erythrocytes. The blood sample containing erythrocytes was mixed with the above erythrocyte treatment solution at a volume ratio of 1:1, and after mixing evenly, the mixture was left to stand at room temperature for 3 hours for performing oxidization and fixation treatments on the erythrocytes.

(4) The erythrocytes subjected to the treatment in step (3) were washed with a PBS buffer at least twice, and then the erythrocytes were suspended in the above preservation solution to obtain erythrocyte simulating particles, which were stored at 2-8° C.

Figure 9:
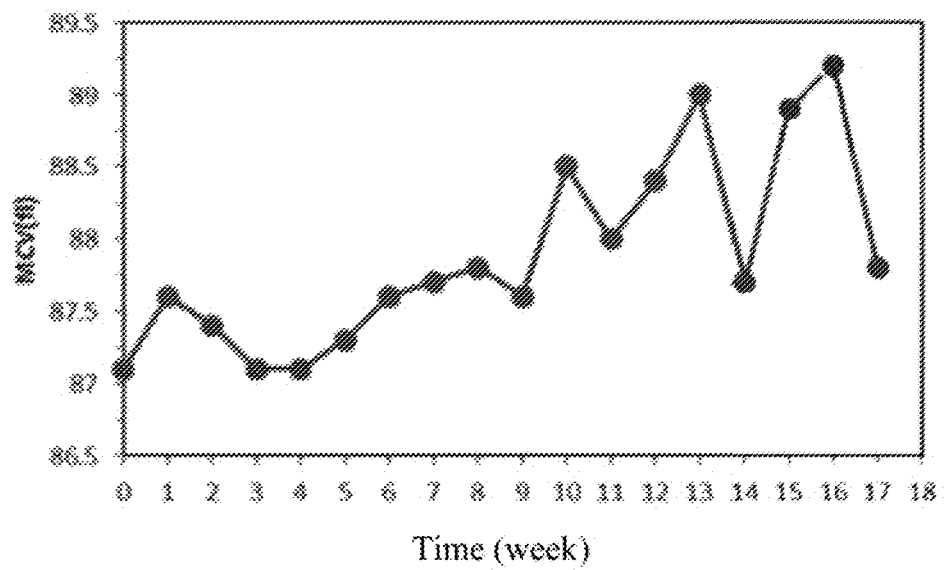
FIG. 9 is a graph of the mean erythrocyte volume over time of erythrocyte simulating particles prepared according to example 8, as continuously measured in 18 weeks.

The erythrocyte simulating particles in example 8 were subjected to an MCV erythrocyte simulating particles were measured at least twice a week, and the MCV measurement results were averaged. The measurement results are as shown in FIG. 9. The MCV measured during the whole measurement period has a range (difference between the maximum and minimum values) of 2.0 fl, and an SD (standard deviation) of 0.58.

Example 9: Treatment Using Sodium Chlorate of about 1 g/L

Erythrocyte simulating particles were prepared according to the following steps.

(1) An erythrocyte treatment solution was prepared according to the table below.

| No. | Name of component | Amount of component |
| --- | --- | --- |
| 1 | Proclin 300 | 3 ml |
| 2 | Sodium chlorate | 1 g |
| 3 | Formaldehyde | 0.5 ml |
| 4 | PBS buffer | 1 L |

The pH was 8.0, and the osmotic pressure was 400 Osm/kg · $H_2O$ (2) A preservation solution was prepared according to the formulation of example 7.

(3) 20 ml of human anticoagulant blood was filtered, centrifuged to remove leukocytes and platelets, and washed with a PBS buffer twice, and the supernatant was discarded, with packed erythrocytes remained, so as to obtain a blood sample containing erythrocytes. The blood sample containing erythrocytes was mixed with the above erythrocyte treatment solution at a volume ratio of 1:1, and after mixing evenly, the mixture was left to stand at room temperature for 3 hours for performing oxidization and fixation treatments on erythrocytes.

(4) The erythrocytes subjected to the treatment in step (3) were washed with a PBS buffer at least twice, and then the erythrocytes were suspended in the above preservation solution to obtain erythrocyte simulating particles, which were stored at 2-8° C.

Figure 10:
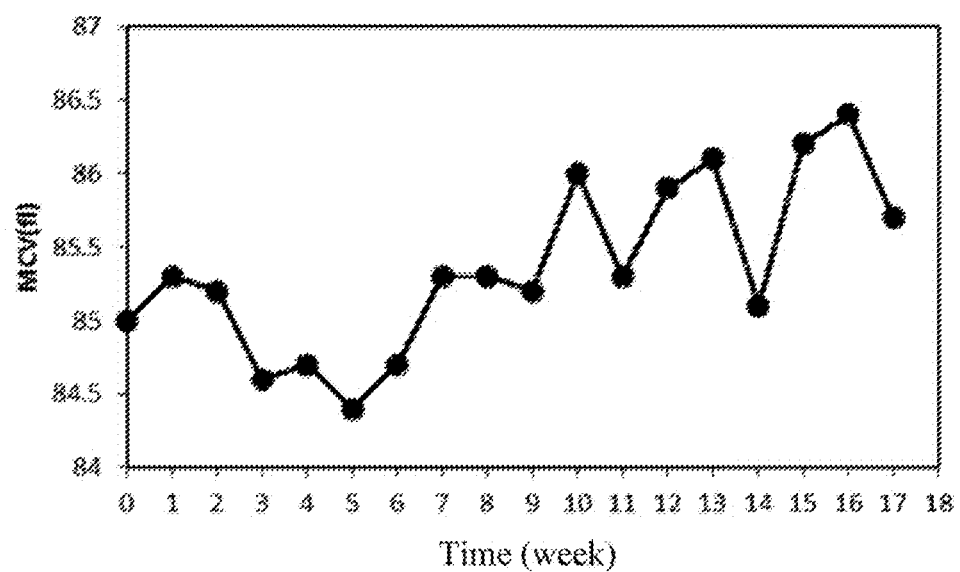
FIG. 10 is a graph of the mean erythrocyte volume over time of erythrocyte simulating particles prepared according to example 9, as continuously measured in 18 weeks.

The erythrocyte simulating particles in example 9 were subjected to an MCV erythrocyte simulating particles were measured at least twice a week, and the MCV measurement results were averaged. The measurement results are as shown in FIG. 10. The MCV measured during the whole measurement period has a range (difference between the maximum and minimum values) of 2.1 fl, and an SD (standard deviation) of 0.66.

Example 10: Treatment Using Sodium Chlorate of about 2 g/L

Erythrocyte simulating particles were prepared according to the following steps.

(1) An erythrocyte treatment solution was prepared according to the table below.

| No. | Name of component | Amount of component |
| --- | --- | --- |
| 1 | Proclin 300 | 3 ml |
| 2 | Sodium chlorate | 2 g |

| No. | Name of component | Amount of component |
| --- | --- | --- |
| 3 | Formaldehyde | 0.5 ml |
| 4 | PBS buffer | 1 L |

The pH was 8.0, and the osmotic pressure was 400 Osm/kg · H$_2$O (2) A preservation solution was prepared according to the formulation of example 7.

(3) 20 ml of human anticoagulant blood was filtered, centrifuged to remove leukocytes and platelets, and washed with a PBS buffer twice, and the supernatant was discarded, with packed erythrocytes remained, so as to obtain a blood sample containing erythrocytes. The blood sample containing erythrocytes was mixed with the above erythrocyte treatment solution at a volume ratio of 1:1, and after mixing evenly, the mixture was left to stand at room temperature for 3 hours for performing oxidization and fixation treatments on erythrocytes.

(4) The erythrocytes subjected to the treatment in step (3) were washed with a HEPES buffer at least twice, and then the erythrocytes were suspended in the above preservation solution to obtain erythrocyte simulating particles, which were stored at 2-8° C.

Figure 11:
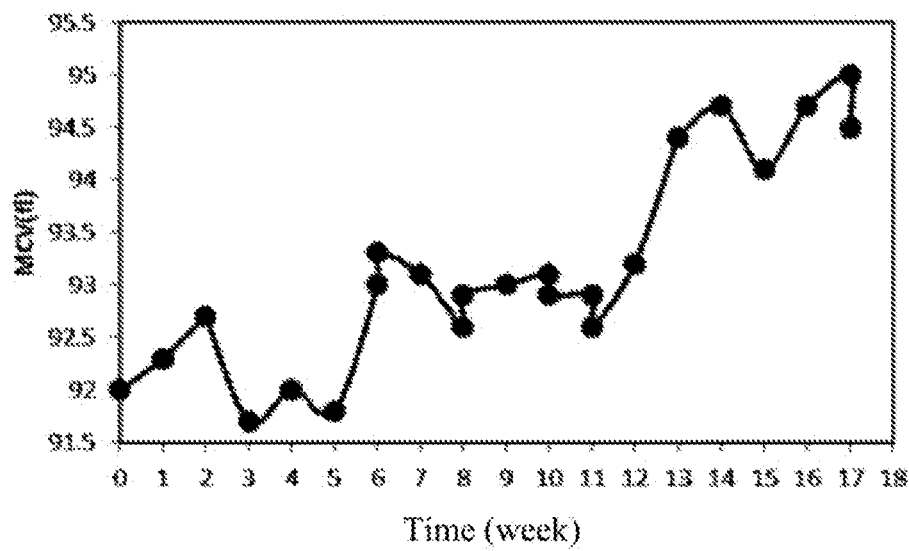
FIG. 11 is a graph of the mean erythrocyte volume over time of erythrocyte simulating particles prepared according to example 10, as continuously measured in 18 weeks.

The erythrocyte simulating particles in example 10 were subjected to an MCV erythrocyte simulating particles were measured at least twice a week, and the MCV measurement results were averaged. The measurement results are as shown in FIG. 11. The MCV measured during the whole measurement period has a range (difference between the maximum and minimum values) of 3.3 fl, and an SD (standard deviation) of 0.97.

Example 11: Quality Control for Blood Cell Analysis

A quality control for blood cell analysis was prepared according to the method below.

Leukocyte simulating particles, platelet simulating particles, and the erythrocyte simulating particles prepared in example 6 and suspended in the preservation solution were mixed at a certain ratio to obtain a quality control for blood cell analysis, which was stored at a low temperature of 2-8° C. The leukocyte simulating particles and the platelet simulating particles used herein may be commercially available products, or may be simulating materials prepared by conventional or known methods, in particular, leukocyte simulating particles of Mindray BR60/B55/B30 and platelet simulating particles of Mindray BR60/B55/B30, both of which are preferably transferred to suspended in the same preservation solution as the erythrocyte simulating particles by washing and centrifugation.

Figure 12:
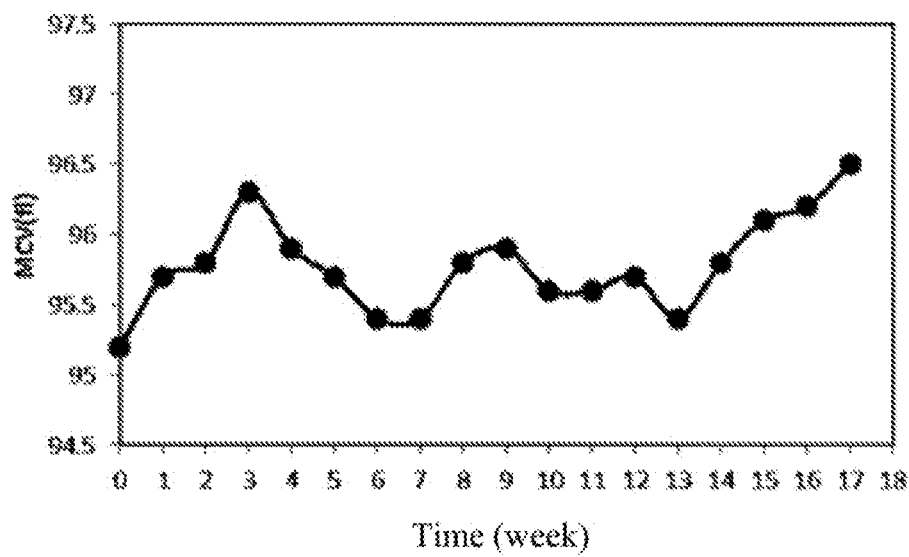
FIG. 12 is a graph of the mean erythrocyte volume over time of a quality control prepared according to example 11, as continuously measured in 18 weeks.

The above quality control for blood cell analysis was subjected to an MCV measurement on a blood cell analyzer continuously for 18 weeks by the blood cell analyzer, in which the quality control was measured at least twice a week, and the MCV measurement results were averaged. The measurement results are as shown in FIG. 12. The MCV measured during the whole measurement period has a range (difference between the maximum and minimum values) of 1.3 fL, and an SD of 0.32.

Figure 13:
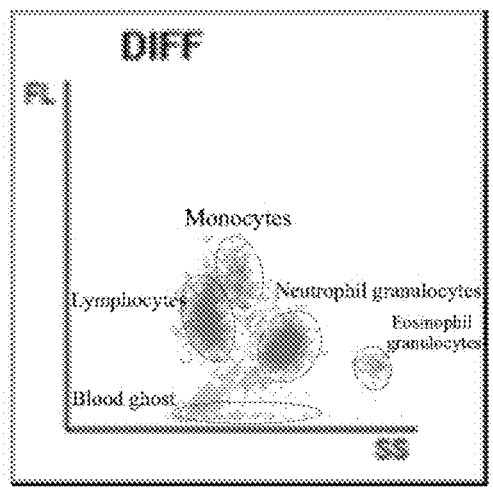
FIG. 13 shows two-dimensional scattered light-fluorescence light scattergrams (a1 and b1) of white blood cells (WBC) and histograms (a2 and b2) of red blood cells (RBC) of freshly collected human anticoagulant blood (a1 and a2) and the quality control (b1 and b2) prepared according to example 11.
Figure 13:
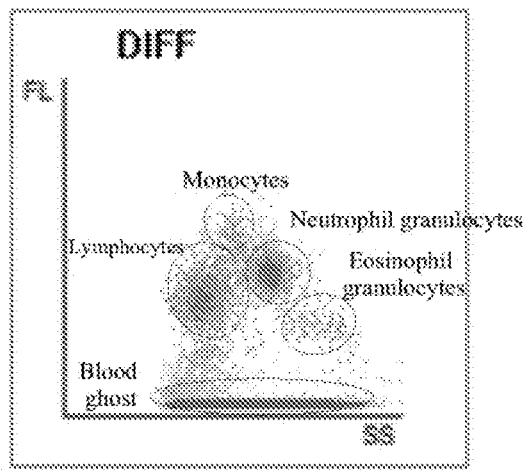
Figure 13:
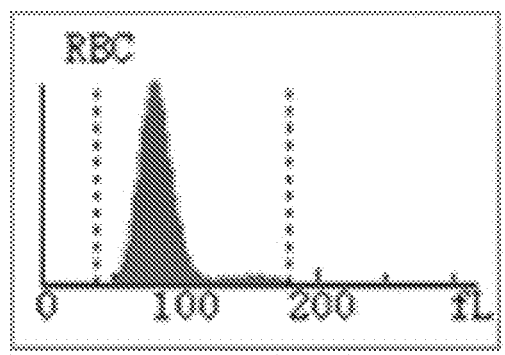
Figure 13:
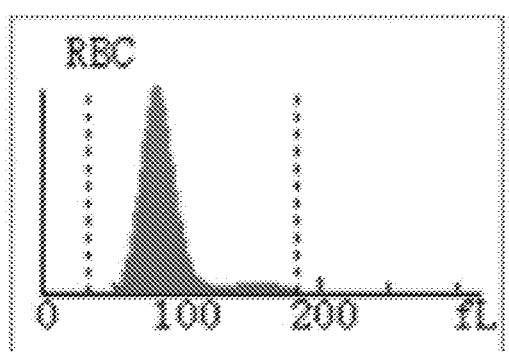

Further, the quality control product of this example and fresh human anticoagulant blood were used as analysis samples and were respectively injected into a blood cell analyzer (Mindray BC6 blood analyzer) for measurement, the results thereof are as shown in FIG. 13. FIG. 13 (a) shows a two-dimensional fluorescence-scattered light scattergram (a1) of WBC and a histogram (a2) of RBC of the fresh blood sample obtained on the blood cell analyzer; and FIG. 13 (b) shows a two-dimensional fluorescence-scattered light scattergram (b1) of WBC and a histogram (b2) of RBC of the quality control (including the leukocyte simulating particles, the platelet simulating particles, and the erythrocyte simulating particles prepared in example 6 and suspended in the preservation solution) for blood cell analysis of this example obtained on the blood cell analyzer.

The results show that, the erythrocyte simulating particles prepared by the method of the disclosure have a volume similar to the erythrocytes in fresh blood, and also have a hemolytic activity similar to the erythrocytes in fresh blood, and therefore, the erythrocyte simulating particles will not affect classification of leukocytes in a DIFF classification scattergram. It is indicated that the quality control containing the erythrocyte simulating particles prepared by the method of the present disclosure behaves, in a blood analyzer, similar to fresh blood.

The description above merely relates to the examples of some of the embodiments of the disclosure, and is not intended to limit the scope of the disclosure. All equivalent structure transformations made by using the contents of the specification and the drawings of the disclosure from the concept of the disclosure, or the direct/indirect applications of the contents in other related technical fields are all included in the patent protection scope of the disclosure.

The invention claimed is:

1. A method for preparing erythrocyte simulating particles, the method comprising:
   performing oxidization and fixation treatments on erythrocytes by using an erythrocyte treatment solution that has a pH of 5.0-9.0 and an osmotic pressure of 300-800 Osm/kg·H$_2$O, wherein the erythrocyte treatment solution contains at least one oxidization agent selected from the group consisting of halogen oxygen acid salts and at least one fixation agent selected from the group consisting of aldehydes or acids; and
   washing the erythrocytes treated by the erythrocyte treatment solution and suspending the same in a preservation solution,
   wherein the at least one oxidization agent has a concentration of 0.01-20 g/L in the erythrocyte treatment solution.

2. The method of claim 1, wherein the at least one oxidization agent is selected from the group consisting of hypohalous acid salts, halous acid salts, halic acid salts and perhalic acid salts of chlorine, bromine and iodine.

3. The method of claim 1, wherein the at least one oxidization agent is a perchlorate, and has a concentration of 8-20 g/L in the erythrocyte treatment solution; or the at least one oxidization agent is a bromate, and has a concentration of 0.25-2 g/L in the erythrocyte treatment solution; or the at least one oxidization agent is a chlorate, and has a concentration of 0.5-2 g/L in the erythrocyte treatment solution.

4. The method of claim 1, wherein the at least one fixation agent is selected from the group consisting of formaldehyde, glutaraldehyde, glyoxal, methylglyoxal, p-trifluoromethyl benzaldehyde, paraformaldehyde, chromic acid, picric acid, tannic acid and acetic acid.

5. The method of claim 1, wherein the at least one fixation agent has a volume concentration of 0.01-0.5 vol % in the erythrocyte treatment solution.

6. A method for preparing erythrocyte simulating particles, the method comprising:
performing an oxidization treatment on erythrocytes by using a first erythrocyte treatment solution that has a pH of 5.0-9.0 and an osmotic pressure of 300-800 Osm/kg·H$_2$O, wherein the first erythrocyte treatment solution contains at least one oxidization agent selected from the group consisting of halogen oxygen acid salts, and the at least one oxidization agent has a concentration of 0.01-20 g/L in the first erythrocyte treatment solution;
performing a fixation treatment on the erythrocytes by using a second erythrocyte treatment solution that has a pH of 5.0-9.0 and an osmotic pressure of 300-800 Osm/kg·H$_2$O, wherein the second erythrocyte treatment solution contains at least one fixation agent selected from the group consisting of aldehydes or acids; and
washing the erythrocytes treated by the first erythrocyte treatment solution and the second erythrocyte treatment solution and suspending the same in a preservation solution.

7. The method of claim 6, wherein the at least one oxidization agent is selected from the group consisting of hypohalous acid salts, halous acid salts, halic acid salts and perhalic acid salts of chlorine, bromine and iodine.

8. The method of claim 1, wherein the preservation solution has a pH of 5.0-9.0 and an osmotic pressure of 300-800 Osm/kg·H$_2$O, and includes 0.01-10 g/L of a preservative and 0.01-5 g/L of a stabilizer.

9. The method of claim 1, wherein the erythrocytes are derived from mammals.

10. The method of claim 2, wherein the at least one oxidization agent is selected from the group consisting of sodium salts and potassium salts of hypochlorous acid, chlorous acid, chloric acid, perchloric acid, bromic acid, iodic acid and periodic acid.

11. The method of claim 10, wherein the at least one oxidization agent is selected from the group consisting of sodium perchlorate, potassium perchlorate, sodium bromate, potassium bromate, sodium chlorate and potassium chlorate.

12. The method of claim 1, wherein the at least one oxidization agent has a concentration of 0.05-10 g/L in the erythrocyte treatment solution.

13. The method of claim 12, wherein the at least one oxidization agent has a concentration of 0.05-5 g/L in the erythrocyte treatment solution.

14. The method of claim 3, wherein the at least one oxidization agent is sodium perchlorate, and has a concentration of 8-20 g/L in the erythrocyte treatment solution; or the at least one oxidization agent is sodium bromate, and has a concentration of 0.25-2 g/L in the erythrocyte treatment solution; or the at least one oxidization agent is sodium chlorate, and has a concentration of 0.5-2 g/L in the erythrocyte treatment solution.

15. The method of claim 8, wherein the preservative is at least one selected from the group consisting of isothiazolinones and aminoglycoside antibiotics, and the stabilizer is selected from the group consisting of imidazolidinyl ureas.

16. The method of claim 9, wherein the erythrocytes are derived from humans.

17. The method of claim 6, wherein the at least one oxidization agent is selected from the group consisting of sodium perchlorate, potassium perchlorate, sodium bromate, potassium bromate, sodium chlorate and potassium chlorate.

* * * * *